US011263340B2

(12) United States Patent
Bachmann et al.

(10) Patent No.: US 11,263,340 B2
(45) Date of Patent: Mar. 1, 2022

(54) PRESENTING HEALTH DATA TO A RESPONDING EMERGENCY MEDICAL SYSTEM

(71) Applicant: Aetna Inc., Hartford, CT (US)

(72) Inventors: Alan Bachmann, Cranberry Township, PA (US); Shannon Gienty, Bristol, CT (US); Anthony Cevoli, Bluebell, PA (US)

(73) Assignee: Aetna Inc., Hartford, CT (US)

(*) Notice: Subject to any disclaimer, the term of this patent is extended or adjusted under 35 U.S.C. 154(b) by 715 days.

(21) Appl. No.: 15/799,537

(22) Filed: Oct. 31, 2017

(65) Prior Publication Data
US 2019/0130127 A1 May 2, 2019

(51) Int. Cl.
G06F 21/62 (2013.01)
G16H 10/60 (2018.01)
G16H 40/20 (2018.01)
G16H 10/20 (2018.01)

(52) U.S. Cl.
CPC ......... G06F 21/6245 (2013.01); G16H 10/60 (2018.01); G16H 40/20 (2018.01); G16H 10/20 (2018.01)

(58) Field of Classification Search
CPC combination set(s) only.
See application file for complete search history.

(56) References Cited

U.S. PATENT DOCUMENTS

| 10,176,541 | B2* | 1/2019 | Chaudhri et al. |
| 10,204,704 | B1* | 2/2019 | Wurst |
| 2002/0016923 | A1* | 2/2002 | Knaus et al. |
| 2006/0287906 | A1* | 12/2006 | McGillin |
| 2008/0133269 | A1* | 6/2008 | Ching |
| 2012/0050047 | A1* | 3/2012 | Kim et al. |
| 2014/0249850 | A1* | 9/2014 | Woodson et al. |
| 2015/0019254 | A1* | 1/2015 | Ibikunle et al. |
| 2016/0014584 | A1* | 1/2016 | Webb |
| 2017/0289350 | A1* | 10/2017 | Philbin |
| 2017/0351834 | A1* | 12/2017 | Cahan et al. |
| 2018/0310159 | A1* | 10/2018 | Katz et al. |
| 2018/0358117 | A1* | 12/2018 | Neagle |
| 2019/0166480 | A1* | 5/2019 | Rauner |

* cited by examiner

Primary Examiner — Michael Tomaszewski
Assistant Examiner — William T. Monticello
(74) Attorney, Agent, or Firm — Leydig, Voit & Mayer, Ltd.

(57) ABSTRACT

A method for presenting health data to a responding emergency medical system (EMS) device includes: (a) registering an EMS profile and a member profile, the member profile to include an option for sharing member information, and the EMS profile to include one or more authorizations for receiving the member information; (b) receiving trigger information including a request for the member information; (c) receiving the member information from one or more sources; (d) packaging the member information in a member care file based on the request for the member information being valid; and (e) providing the member care file to the EMS device.

20 Claims, 4 Drawing Sheets

PRESENTING HEALTH DATA TO A RESPONDING EMERGENCY MEDICAL SYSTEM

BACKGROUND

Emergency medical system personnel respond to a variety of situations with sometimes incomplete or erroneous information. Emergency medical system personnel may include, for example, federal, state, and local governmental and nongovernmental emergency medical (including hospital emergency facilities), and related personnel, agencies, and authorities. The emergency medical system personnel are usually first responders tasked with care of an individual or individuals in distress, providing temporary care until the individual or individuals can be transferred to a primary care physician, a hospital, a clinic, and/or the individual or individuals feel better.

In emergency situations, individuals calling 911 are treated on a reactionary, best effort care method by the first responders. In some cases, the reactionary method causes unnecessary delays in care, while first responders attempt to get information from a patient in need or from a caller or caregiver in proximity to the patient. Sometimes the information obtained by the first responders from the caller or caregiver is inaccurate and incomplete communication. Sometimes, cautionary care (or a lower standard of care) is administered to a patient due to the first responder's need to make and use assumptions about the patient's medications, insurance coverage, and healthcare providers in the area. For example, patients may be taken by first responders to multiple healthcare providers before ending up at the right facility. This multi-hop during emergencies further delays proper care.

SUMMARY

An embodiment of the disclosure provides a method for presenting health data to a responding emergency medical system (EMS) device. The method is performed by a server including a processor and a non-transitory computer readable medium with computer-executable instructions stored thereon, such that when the instructions are executed by the processor, the server facilitates the method comprising: (a) registering an EMS profile and a member profile, the member profile to include an option for sharing member information, and the EMS profile to include one or more authorizations for receiving the member information; (b) receiving trigger information including a request for the member information; (c) receiving the member information from one or more sources; (d) packaging the member information in a member care file based on the request for the member information being valid; and (e) providing the member care file to the EMS device.

Another embodiment of the disclosure provides a server for presenting health data to a responding emergency medical system (EMS) device. The server includes a processor and a non-transitory computer readable medium containing instructions stored thereon, such that when the instructions are executed by the processor, the server performs the method comprising: (a) registering an EMS profile and a member profile, the member profile to include an option for sharing member information, and the EMS profile to include one or more authorizations for receiving the member information; (b) receiving trigger information including a request for the member information; (c) receiving the member information from one or more sources; (d) packaging the member information in a member care file based on the request for the member information being valid; and (e) providing the member care file to the EMS device.

Yet another embodiment of the disclosure provides an emergency medical system (EMS) device for receiving health data from a healthcare server. The device includes a processor and a non-transitory computer readable medium containing instructions stored thereon, such that when the instructions are executed by the processor, the device performs the method comprising: (a) registering an EMS profile with the healthcare server, the EMS profile to include one or more authorizations for receiving member information associated with a member profile; (b) providing trigger information to the healthcare server, the trigger information to include a request for the member information; and (c) based on the request for member information being valid, receiving a member care file from the healthcare server, wherein, the member care file includes the member information packaged from one or more sources, and the member profile includes an option for sharing member information.

DETAILED DESCRIPTION

Figure 1:
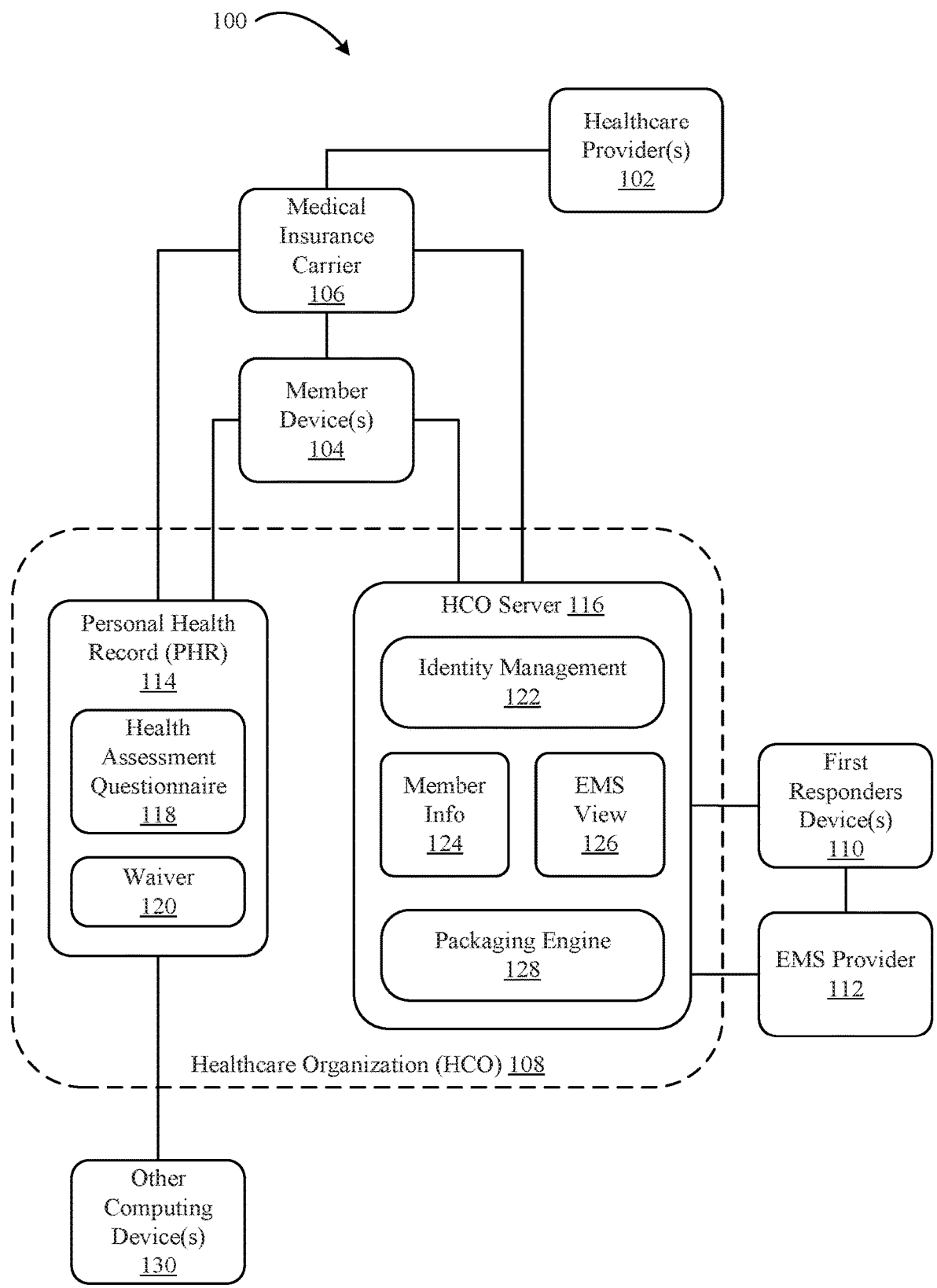
FIG. 1 illustrates a system for presenting health data to a responding emergency medical system personnel, according to an embodiment of the disclosure.

Embodiments of the disclosure provide an advantage by empowering first responders with confidential health information about a patient in near real-time. The provision of the health information may enable first responders, who are en route to the patient, to begin interacting with the patient (or a caller responsible for the patient) in order to provide the best care.

Embodiments of the disclosure provide further advantages that may revolutionize Emergency Medical System (EMS) abilities. In a first aspect, receiving a briefing for every patient will enable first responders to provide a more direct and better care. In some cases, a more direct care involves reducing the amount of time to communicate a patient's health information, since depending on the patient's medical status and emergency, every second may matter. In some cases, a better care involves reducing mistakes, guessing, and waste, thus, enabling the patient to be cared for in a more targeted manner, and having a more complete health history facilitates these measures. A more direct and better care may be beneficial in situations when first responders are caring for a patient who is unable to talk or unable to communicate while the first responders are in route. An unconscious patient is an example of such a patient.

In a second aspect, EMS abilities may be revolutionized as a result of efficiency improvements, such as, less time on scene, confirmed provider destination, and when appropriate, leveraging non-emergency transportation options. In some cases, operating costs that counties, local governments, or regions bear to have first responders services, can be reduced. Reduced operating costs may lead to efficiently attacking a nationwide EMS insolvency epidemic; and the cost savings may be reallocated to fund or improve upon the number of EMS locations in order to help people find care. Reduced operating costs may also lead to lowering costs of services and chargebacks billed to insurance companies. Reduced operating costs may also result from shifting first responders from collecting patient data to validating provided data, thus, improving patient data accuracy and reducing time spent by first responders on scene before administering care.

In a third aspect, EMS abilities may be revolutionized, since first responders can also leverage validated patient information to eliminate some of the manual EMS efforts in performing outreach to people/facilities and expediting the documentation process for EMS delivered care (getting them back in service faster with a higher degree of factual notes). First responders may no longer have to rely on long handwritten notes, which may contain errors or may be illegible.

In an embodiment of the disclosure, a system is provided that performs the following: enrollment of first responders to access patient health data on-demand, providing real-time collection, aggregation, and enrichment of data from insurance (or payer) systems and secure packaging of health data into consumable fashion for EMS personnel.

FIG. 1 illustrates a system 100 for presenting health data to a responding emergency medical system personnel using a first responders device(s) 110, according to an embodiment of the disclosure. The system 100 includes one or more healthcare provider(s) 102, a medical insurance carrier 106, one or more member device(s) 104, third party or other computing device(s) 130, an EMS provider 112, a healthcare organization (HCO) 108, and one or more first responders device(s) 110. For ease of description, the singular form will be used for the healthcare provider(s) 102, member device(s) 104, other computing device(s) 130, and the first responders device(s) 110 by default, and the plural form will be used when appropriate.

The member device 104, other computing device 130, and the first responders device 110 are computing devices used by an individual. Example computing devices include mobile devices, for example, a smartphone, a tablet, a phablet, a smart watch, a fitness tracking device, and so on. Computing devices may also include larger devices, for example, a smart television, a laptop computer, a desktop computer, a server, and so on.

The healthcare providers 102 have computing devices that allow provision of information to the medical insurance carrier 106. The healthcare providers 102 may be hospitals, pharmacies, clinics, temporary care facilities, and so on. The healthcare providers 102 may submit claims to the medical insurance carrier to request payment for diagnosis, treatment, or other services provided to a patient. The healthcare providers 102 may also provide information related to laboratory data of the patient. The healthcare providers 102 may also provide information related to pharmaceuticals or other drugs prescribed or recommended to the patient.

In an embodiment, the medical insurance carrier 106 may aggregate health information obtained from healthcare providers 102 with health information obtained from caregivers, family members, or friends of the patient, and the patient through member device 104.

The HCO 108 maintains a personal health record (PHR) 114 for a patient (or member) associated with the HCO 108. The HCO 108 also includes an HCO server 116 for presenting health data to a responding emergency medical system personnel. The PHR 114 may be populated with information from the medical insurance carrier 106 or the member device 104. The member device 104 may be a wearable electronic device that provides one or more vital signs, for example, heart rate, temperature, blood pressure, and so on. The member device 104 may also provide health information of the member through a health assessment questionnaire 118. The health assessment questionnaire 118 provides questions to the member, and the member provides answers to those questions, allowing the population of the PHR 114. In some embodiments, the health assessment questionnaire 118 is activated on a yearly time interval, allowing the member device 104 to update information in the PHR 114 once a year. The yearly time interval is used as an example. Other timeframes shorter than a year, for example, months, may be used, or no timeframes may be enforced, allowing the member to provide health information at any point in time. The PHR 114 may also include a waiver 120, which identifies healthcare providers 102 that the HCO 108 is allowed to share information contained in the PHR 114 with. The PHR 114 may be downloaded into various file formats, for example, a text file, a portable document format, or the PHR 114 may be uploaded to a cloud server in the other computing devices 130 for third party analysis.

The HCO server 116 provides a service that allows sharing of health data to an EMS personnel. The HCO server 116 receives information from member devices 104 and/or medical insurance carrier 106. The member devices 104 may allow the member to register and update a member profile associated with the service that allows sharing of the health data. The medical insurance carrier 106 may provide insurance information for the member, including member benefits and participating providers in the member's insurance plan. The HCO server 116 includes an identity management engine 122, a member information engine 124, an EMS view engine 126, and a packaging engine 128. An engine identifies software components running on the HCO server 116 for providing one or more services according to embodiments of the disclosure. The identity management engine 122 tracks the waiver 120 and contracts established with the EMS provider 112. The identity management engine 122 is involved with enrollment and authentication processes for the EMS provider 112 and the first responders device 110. The member information engine 124 aggregates information of the member, for example, medical history, vitals, participating providers, and so on, from the PHR 114 and the medical insurance carrier 106. The EMS view engine 126 provides limited time access for an approved first responders device to access the member's health data. The EMS view engine 126 may also track access requests from the first responders device 110 or the EMS provider 112. The EMS view engine 126 may also identify the member whose information is being sought. The packaging engine 128 aggregates health data for the member, generates a data expiration date for the health data, and formats the health data into a file format that may be consumed by the first responders device 110. The file format may include a HIPAA HL7 continuity of care document (CCD).

In some embodiments, the HCO 108 and the medical insurance carrier 106 are the same organization.

Figure 2:
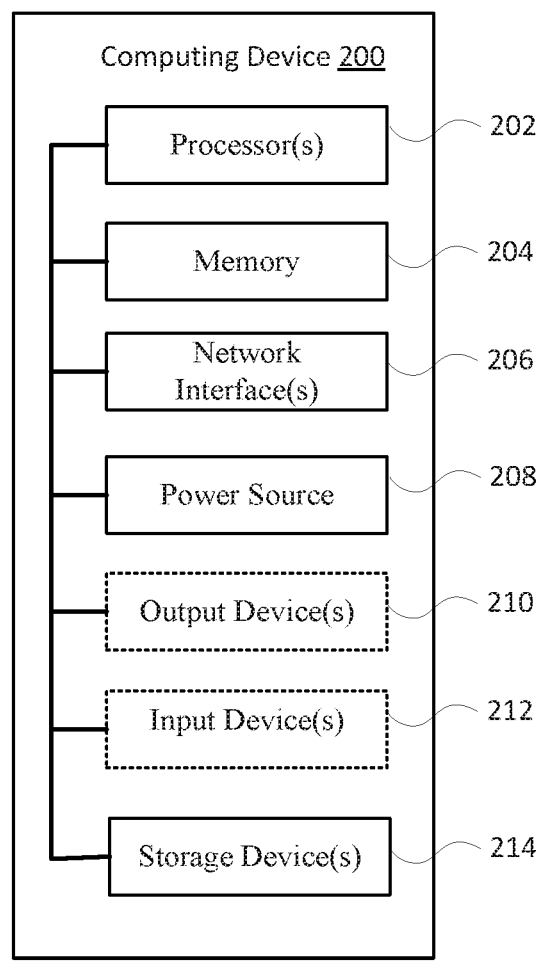
FIG. 2 is a block diagram illustrating components of a computing device according to some example embodiments.

FIG. 2 is a block diagram illustrating basic hardware components of a computing device 200 that may be used at the healthcare provider 102, the medical insurance carrier 106, the EMS provider 112, and the HCO 108, according to some example embodiments. The computing device 200 may also be used as the member device 104, the other computing devices 130, and the first responders devices 110, and one or more computing devices 200 may be used to realize the HCO server 116 and to store the PHR 114.

Computing device 200 may include one or more processors 202, memory 204, network interfaces 206, power source 208, output devices 210, input devices 212, and storage devices 214. Each component provided is interconnected physically, communicatively, and/or operatively for inter-component communications in order to realize functionality ascribed to the one or more entities in FIG. 1. To simplify the discussion, the singular form will be used for all components identified in FIG. 2, when appropriate, but the use of the singular does not limit the discussion to only one of each component. For example, multiple processors may implement functionality attributed to processor 202.

Processor 202 is configured to implement functions and/or process instructions for execution within the device 200. For example, processor 202 executes instructions stored in memory 204 or instructions stored on a storage device 214. In certain embodiments, instructions stored on storage device 214 are transferred to memory 204 for execution at processor 202. Memory 204, which may be a non-transient, computer-readable storage medium, is configured to store information within the device 200 during operation. Memory 204 may include random access memories (RAM), dynamic random access memories (DRAM), and static random access memories (SRAM). Memory 204 also maintains program instructions for execution by the processor 202 and serves as a conduit for other storage devices (internal or external) coupled to the device 200 to gain access to processor 202.

Storage device 214 includes one or more non-transient computer-readable storage media. Storage device 214 is provided to store larger amounts of information than memory 204, and in some instances, configured for long-term storage of information. Non-limiting examples of non-volatile storage elements include floppy discs, flash memories, magnetic hard discs, optical discs, or solid state drives.

Network interfaces 206 are used to communicate with external devices and/or servers. The computing device 200 may comprise multiple network interfaces 206 to facilitate communication via multiple types of networks. Network interfaces 206 may comprise network interface cards, such as Ethernet cards, optical transceivers, radio frequency transceivers, or any other type of device that can send and receive information. Non-limiting examples of network interfaces 206 include radios compatible with several Wi-Fi standards, 3G, 4G, Long-Term Evolution (LTE), Bluetooth®, etc.

Power source 208 provides power to the device 200. For example, the device 200 may be battery powered through rechargeable or non-rechargeable batteries utilizing nickel-cadmium or other suitable material. Power source 208 may include a regulator for regulating power from the power grid in the case of a device plugged into a wall outlet.

The device 200 may also be equipped with one or more output devices 210. Output device 210 is configured to provide output to a user using tactile, audio, and/or video information. Examples of output device 210 may include a display (cathode ray tube (CRT) display, liquid crystal display (LCD) display, LCD/light emitting diode (LED) display, organic LED display, etc.), a sound card, a video graphics adapter card, speakers, magnetics, or any other type of device that may generate an output intelligible to a user of the device 200.

The device 200 may also be equipped with one or more input devices 212. Input devices 212 are configured to receive input from a user or the environment where the device 200 resides. In certain instances, input devices 212 include devices that provide interaction with the environment through tactile, audio, and/or video feedback. These may include a presence-sensitive screen or a touch-sensitive screen, a mouse, a keyboard, a video camera, microphone, a voice responsive system, or any other type of input device.

The hardware components described thus far for the device 200 are functionally and communicatively coupled to achieve certain behaviors. In some embodiments, these behaviors are controlled by software running on an operating system of the device 200.

Figure 3:
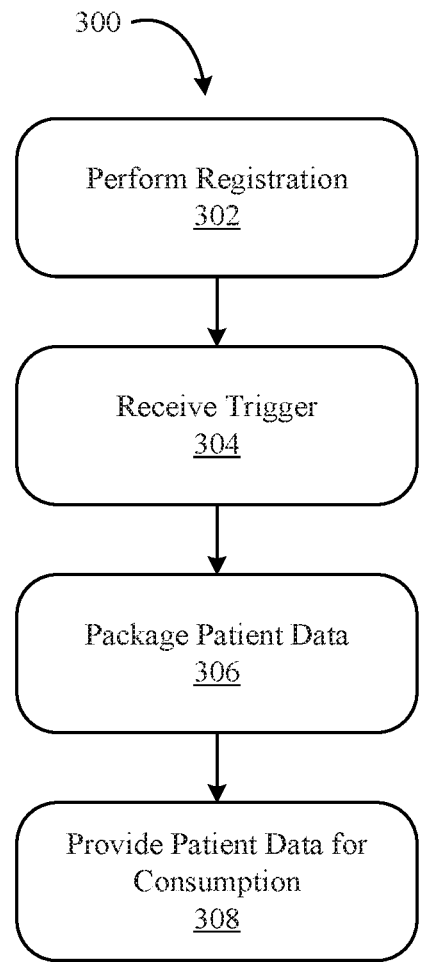
FIG. 3 is a flow diagram illustrating a process for presenting health data according to an embodiment of the disclosure.

FIG. 3 is a flow diagram illustrating a process 300, performed by the HCO server 116, for presenting health data to the first responders device 110, according to an embodiment of the disclosure. At step 302, the HCO server 116 registers an EMS provider 112. The EMS provider 112 may provide information on one or more organizations associated with the EMS provider 112. For example, the EMS provider 112 may be a county running an EMS system that includes one or more independent organizations, and each organization may have one or more first responders. The county may register all organizations in its EMS system. The county may further register in its EMS system all employees in the organizations that may receive a member's health data. The HCO server 116 creates an EMS profile for the EMS provider 112, receiving from the EMS provider 112 one or more organization names associated with the EMS provider 112, staff names, staff roles and titles, and/or an organization location. The EMS profile may be organized by first responders profiles, where a first responders profile is a profile set up for each organization under the EMS provider 112. Each EMS profile may include, for each first responder, authorizations for receiving member information. In some embodiments, the EMS profile is temporarily valid, therefore, to keep the EMS profile active past the profile validity period, the EMS provider 112 re-registers. The EMS profile may be kept up to date by the EMS provider 112 informing the HCO server 116 of any first responders staff no longer employed or informing of any first responders staff newly employed.

At step 302, a member profile may also be registered. Registration of the member profile may include receiving an option from the member device 106 indicating that the member authorizes sharing health data or member information with an emergency service provider. The member information may include medical history, medical conditions, medical insurance, work address, home address, provider preferences, medication, and/or vital signs. In some embodiments, the authorization for sharing health data or member information is only temporarily valid. The member may be prompted to re-authorize, for example, in a year, two years, five years, and so on.

At step 304, the HCO server 116 receives trigger information from either a first responders device 110 or an EMS provider 112. The trigger information includes a request for the HCO server 116 to provide member information. If the EMS provider 112 sends the trigger information, the trigger information may include patient name, a timestamp for when an emergency alert involving the patient was received, and an EMS crew assigned to service the emergency alert. If the first responders device 110 sends the trigger information, the trigger information may not need to include the EMS crew. The first responders device 110 may be authenticated by associating the first responders device 110 with at least one first responders profile in the EMS profile.

During authentication, the first responder's device 110 or the EMS provider 112 may send patient identifying information, including, for example, name, age, or the patient's photograph. The HCO server 116 may then verify the information received. The HCO server 116 rejects incorrect or insufficient information from any EMS staff, and he/she will be responsible for providing additional requested details back to the HCO server 116 in order to either complete authentication or register. When an EMS provider 112 is registered, a business associate agreement is created, thereby satisfying the Health Insurance Portability and Accountability Act (HIPAA) requirement for information sharing. Upon authentication of first responders, the HCO server 116 may send out a confirmation to the EMS provider 112 as well as to the first responders device 110 that they have been authenticated to access member health data.

At step 306, the HCO server 116 packages the member information in a member care file based on the EMS provider 112 and/or the first responders device 110 providing a valid request. A request is valid if the first responders device 110 or the EMS profile is valid. The HCO server 116 may collect different information from one or more sources. In one example, the HCO server 116 may aggregate institution information, including current hospital availability and/or treatment specialties proximate to the patient. The HCO server 116 may update the member information based on the institution information.

At step 306, the HCO server 116 may perform anomaly detection, removing incorrect information in the health data or member information to obtain verified member information. Anomaly detection may be accomplished by comparing data obtained from multiple data sources. Incorrect data is identified across all data sources. For example, if two out of three sources do not match, the data is marked as incorrect.

At step 306, the HCO server 116 may utilize cognitive services supported through machine learning capabilities. For example, the HCO server 116 may review milestone data, for example, member medical history, problems, and procedures, in the member information to develop trend information. Cognitive services can examine massive data volumes and pull out likely issues and risk factors; and can also associate active prescribed medications with conditions/treatments.

In an example, the HCO server 116 may utilize machine learning to scan through unstructured or non-standardly formatted medical claims and medical records. During the scan, the HCO server 116 may identify "entities" which are medically significant/meaningful conditions. Using cognitive services, the HCO server 116 takes those entities and looks for relationships with other entities and details already known about the member from the PHR 114. For example, blood tests from multiple labs (vendors) could be scanned, and the HCO server 116 can gather that an increased chance of some disease is likely based on comparing the member's history to a known (de-identified) population for which the HCO server 116 has data. In some cases, using embodiments of the disclosure, small factors (aka entities) can be up to 78% accurate in performing diagnoses as compared to a human with the same information, which gets an 80% accuracy with a much longer timeframe. With more data to train the machine learning capacity of the HCO server 116, it is likely that accuracy levels will improve beyond humans with an expert skill level, with an even shorter timeframe.

At step 306, the HCO server 116 may scrub medically irrelevant data from the member information. Medically irrelevant data may be determined based on age of the data. For example, a patient's acne treatment from 20 years ago may be deemed irrelevant. The HCO server 116 may also identify medically relevant data in the member information.

For example, the patient's immunization may be identified as no longer being effective due to the last time the immunization was received by the patient. The HCO server 116 may determine that the patient should get a tetanus shot based on the last time the patient had a tetanus shot. The HCO server 116 may receive insights from data gathered from news sources or advisories. The information from advisories may indicate that the area the patient is located in is associated with one or more medical issues. For example, the HCO server 116 may receive information indicating that the area the patient is located in has a high risk for opiate addiction.

The HCO server 116 may identify relatability factors in the member information. In an example, the HCO server 116 may provide additional information such as the patient preferring to be addressed by his/her middle name. This may speed up communication. In some cases, a member's preferred providers are identified from the member's profile, and the HCO server 116 may determine working hours for the preferred providers. The member information processed at step 306 using one or more of the various activities may then be packaged in the member care file, for example, a HIPAA CCD file. As such, the HIPAA CCD may indicate a patient's medical problems, procedures, family history, social history, payers, advance directives, alerts, medications, immunizations, medical equipment, vital signs, function statistics, results, encounters, and plan of care.

At step 308, the HCO server 116 provides the member care file to the first responders device 110 or the EMS provider 112. Access to the member care file may be valid for a limited amount of time.

Figure 4:
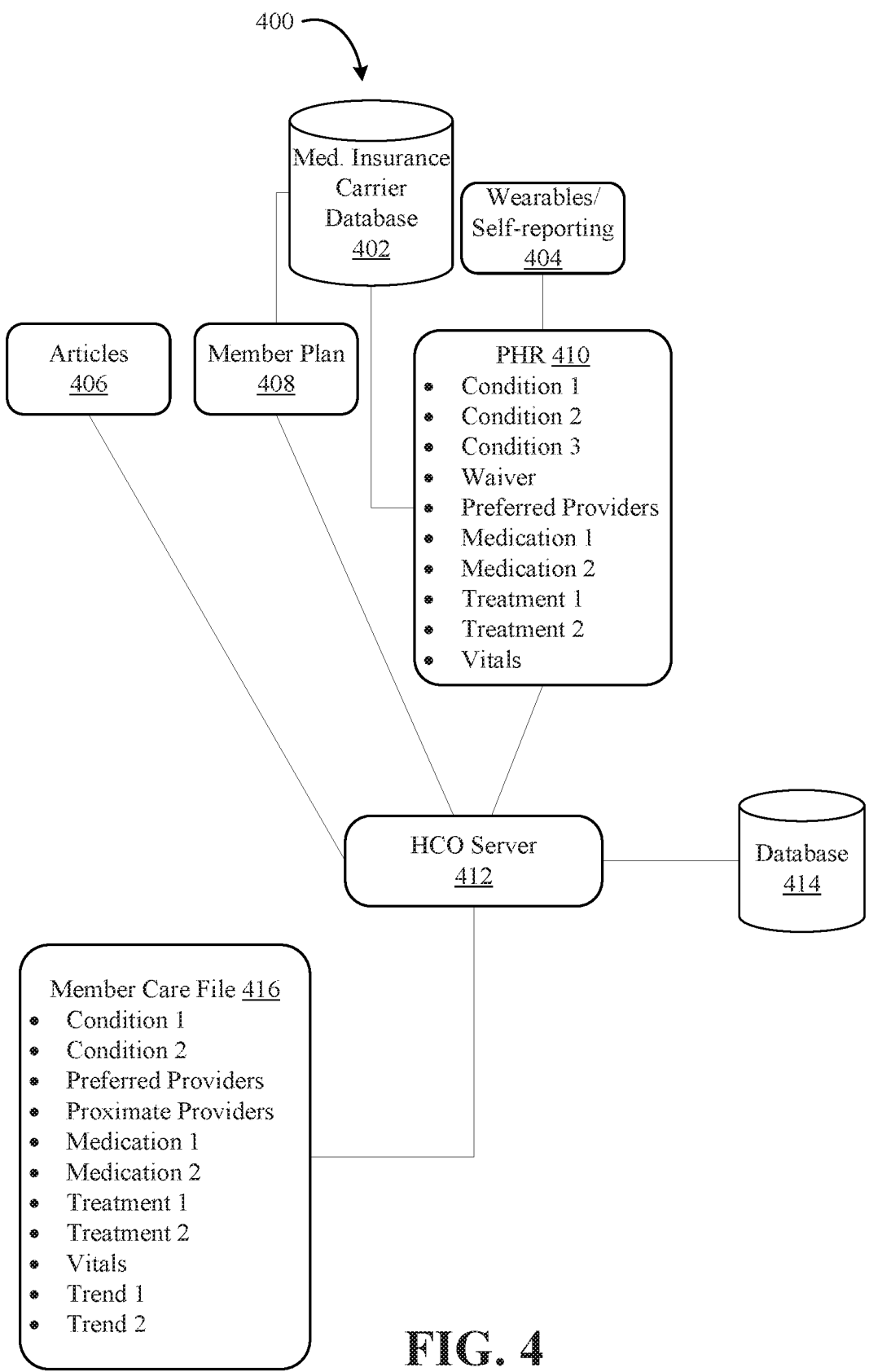
FIG. 4 is a block diagram illustrating a system for presenting health data according to an embodiment of the disclosure.

FIG. 4 illustrates a system 400 for presenting health data according to an embodiment of the disclosure. The system 400 is analogous to that of system 100, for example, HCO server 412 is an embodiment of HCO server 116. A PHR 410 of a member (or patient) is populated using information obtained from a medical insurance carrier database 402, wearable devices and member self-reporting 404. The PHR 410 includes medical conditions, a waiver, the member's preferred providers, medications, treatments undergone, and vitals information. The HCO server 412 has access to the PHR 410, and using information obtained from articles 406, insurance plan information 408, and outside information in database 414, the HCO server 412 is able to generate the member care file 416 for an EMS crew.

The HCO server 412 may determine that Condition 3 in the PHR 410 is not medically relevant and does not include it in the member care file 416. The HCO server 412 may make this determination by checking that Condition 3 is a childhood medical condition that the member suffered from as a child and is a dormant medical condition that does not cause complications in adulthood, based on outside information obtained from database 414. The HCO server 412 may also determine, from outside information in database 414, the nearest healthcare facilities to the member and include Proximate Providers in the member care file 416.

Using cognitive services, the HCO server 412 may determine one or more trends to be included in the member care file 416. Using outside information obtained from database 414, the HCO server 412 may identify that individuals with Condition 1 taking Medication 2 are prone to having adverse effects to a Medication 4. Thus, the HCO server 412 may include Trend 1 indicating a percentage chance that the member may not perform well under Medication 4. The HCO server 412 may also determine, based on articles 406, that individuals in the neighborhood of the member have a higher percentage of Condition 5 compared to individuals of another population set. Using this information, the HCO server 412 may retrieve medical information from a population in the neighborhood of the member and generate Trend 2 to determine how likely the member is at risk for Condition 5. In this example, the development of the trend information leverages population data accessible by the HCO server 412, since the HCO server 412 has access to multiple personal health records and can apply machine learning to make predictions based on one or more factors.

Embodiments of the disclosure may be used to solve a problem where there is a lack of information to EMS personnel, which may cause a delay in patient care and accrue avoidable expenses, such as, multiple ambulance trips.

With some embodiments of the disclosure, members or patients may authorize the sharing of their health information by providing access to historical and recent medical records in a format that medical responders can easily understand. An example of such a format is a mature HIPAA CCD format. Members may also be able to see who has requested access and for how long that access was granted.

Some embodiments provide sensitive data sharing that may be intelligently combined, controlled, and tracked when being used for emergency situations. By having a system for caregivers to contribute to, as well as access the sensitive information in order to answer routine questions as part of the standard treatment procedures, making better decisions and providing care is promoted.

In some embodiments, a member or patient can register himself/herself, assign a delegate (for example, their doctor or doctor's network), or authorize their medical insurance payer (or carrier) to provide details about their health, family, and insurance in the case of an emergency. This information can then be presented in a manner best designed for EMS personnel or EMS units responding to an emergency call, for example, a 911 call.

Embodiments of the disclosure may address one or more problems. Many communities in the U.S. may be able to better keep local EMS units funded. In conventional practice, EMS units take more calls in the hope that patients have insurance, and this practice is risky. Additionally, reciprocal agreements with other nearby EMS units may affect ability to forecast income. Currently, when a patient gets picked up by an ambulance, the EMS first responders crew member does not have the patient's medical history or records, and this may delay and adversely impact patient care. Adverse patient care impact is present especially if the patient cannot communicate or does not speak the same language as the first responders crew on-site. The sooner that the first responders knows that the patient needs a translator or translating services, the better the care.

Embodiments of the disclosure address a second problem of obtaining medical information of a patient. Currently, there is no system for efficiently providing medical information of the patient. Patients do not print out paper copies of their medical information to carry in their wallets/purses. Even if patients had paper copies, these copies would be worthless if not on the patient at a time of emergency.

Embodiments of the disclosure address a third problem of determining healthcare providers that specialize in the patient's care. Currently, patients do not carry a cheat sheet of hospitals and the hospitals' specializations, so that they can properly advise the paramedics where to go. This lack of information results in the ambulance taking the patient to the EMS unit's preferred hospital. The EMS unit may not be up to date on the specialties of each hospital, proximity to those hospitals, and more importantly, if the patient's insurance participates with the hospital. The ambulance services may get called back to take the patient to another hospital because the patient's insurance covers treatment at a different hospital. The EMS unit may be financially happy to charge the patient and the insurance company for two rides, but the patient is delayed services and may be bogged down with additional paperwork and co-pays. The insurance company incurs additional expense for a preventable situation. The first responders addressing the patient's needs becomes unavailable for a longer period of time, being unable to take other calls during the second trip, thus, straining the EMS unit's resources.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for presenting health data to a responding emergency medical system (EMS) device, the method performed by a server including a processor and a non-transitory computer readable medium with computer-executable instructions stored thereon, such that when the instructions are executed by the processor, the server facilitates the method comprising:
- registering, by the server, a member profile based on receiving, from a member device, information indicating an option for sharing member information associated with a member;
- registering, by the server, an EMS profile using the EMS device, wherein the EMS profile includes one or more authorizations for receiving the member information associated with the member;
- receiving, from the EMS device and by the server, trigger information including a request for the member information associated with the member;
- receiving, by the server, medical information associated with the member from one or more sources, wherein the medical information comprises non-standardized data;
- converting, by the server, the non-standardized data into standardized data, wherein the standardized data comprises one or more trends associated with treatments or conditions associated with the member, wherein converting the non-standardized data into the standardized data comprises:
  - identifying entities associated with one or more medically significant conditions based on utilizing machine learning to scan through the non-standardized data;
  - performing diagnoses based on the identified entities to determine the one or more medically significant conditions associated with the member; and
  - determining the one or more trends based on the identified entities, the one or more medically significant conditions, and a personal health record associated with the member;
- based on the request for the member information being valid, generating, by the server and using the standardized data, a member care file comprising updated member information, wherein the updated member information includes the one or more trends; and
- providing, by the server, the member care file to the EMS device in real time so that a user of the EMS device has immediate access to the member care file.

2. The method according to claim 1, wherein the EMS profile includes a first responders profile, wherein the first responders profile includes an organization name, a staff name, a staff role, and/or an organization location.

3. The method according to claim 2, further comprising: authenticating the EMS device by associating the first responders profile with the EMS device.

4. The method according to claim 1, wherein the non-standardized data comprises non-standardized medical claims and medical records, and wherein the member information further includes at least one of medical history, medical insurance, work address, home address, provider preferences, medication, and vital signs.

5. The method according to claim 1, wherein the EMS profile is valid only for a limited time period.

6. The method according to claim 1, wherein the request for the member information is valid only for a limited time period.

7. The method according to claim 1, wherein receiving the trigger information comprises:
- receiving, from the EMS device, the trigger information, wherein
- the trigger information further includes at least one of a timestamp and an EMS crew comprising the user.

8. The method according to claim 1, further comprising:
- aggregating institution information including current hospital availability and/or treatment specialties;
- providing, to the EMS device, the institution information; and
- updating the member information based on the institution information and the one or more trends.

9. The method according to claim 1, further comprising:
- logging an attempt in an access log after receiving the trigger information.

10. The method according to claim 1, wherein generating the member care file comprises:
- performing anomaly detection and removing incorrect information in the member information to obtain verified member information;
- scrubbing medically irrelevant data from the verified member information;
- identifying medically relevant data in the verified member information; and
- packaging the verified member information, the medically relevant data, and the one or more trends in the member care file.

11. The method according to claim 10, wherein generating the member care file further comprises:
- identifying relatability factors in the member information; and
- packaging the relatability factors in the member care file.

12. The method according to claim 10, wherein,
- receiving the member information from the one or more sources includes receiving advisories from news sources, and
- generating the member care file further includes packaging the advisories in the member care file.

13. A server for presenting health data to a responding emergency medical system (EMS) device, the server including a processor and a non-transitory computer readable medium containing instructions stored thereon, such that when the instructions are executed by the processor, the server performs the method comprising:
- registering a member profile based on receiving, from a member device, information indicating an option for sharing member information;
- registering an EMS profile using the EMS device, wherein the EMS profile includes one or more authorizations for receiving the member information associated with the member;
- receiving, from the EMS device, trigger information including a request for the member information;
- receiving medical information associated with the member from one or more sources, wherein the medical information comprises non-standardized data;
- converting the non-standardized data into standardized data, wherein the standardized data comprises one or more trends associated with treatments or conditions associated with the member, wherein converting the non-standardized data into the standardized data comprises:
  - identifying entities associated with one or more medically significant conditions based on utilizing machine learning to scan through the non-standardized data;
  - performing diagnoses based on the identified entities to determine the one or more medically significant conditions associated with the member; and determining the one or more trends based on the identified entities, the one or more medically significant conditions, and a personal health record associated with the member;

based on the request for the member information being valid, generating, using the standardized data, a member care file comprising updated member information, wherein the updated member information includes the one or more trends; and providing the member care file to the EMS device in real time so that a user of the EMS device has immediate access to the member care file.

14. The server according to claim 13, wherein the EMS profile includes at least one first responders profile, wherein the first responders profile includes an organization name, a staff name, a staff role, and/or an organization location.

15. The server according to claim 14, further performing the method comprising:

authenticating the EMS device by associating the at least one first responders profile with the EMS device.

16. The server according to claim 13, wherein the non-standardized data comprises non-standardized medical claims and medical records, and wherein the member information further includes at least one of medical history, medical insurance, work address, home address, provider preferences, medication, and vital signs.

17. The server according to claim 13, wherein, the EMS profile is valid only for a limited time period, and the request for the member information is valid only for a limited time period.

18. The server according to claim 13, wherein receiving the trigger information comprises:

receiving, from the EMS device, the trigger information, wherein the trigger information further includes at least one of a timestamp and an EMS crew comprising the user.

19. A non-transitory computer-readable medium having processor-executable instructions stored thereon, wherein the processor-executable instructions, when executed, facilitate:

registering a member profile based on receiving, from a member device, information indicating an option for sharing member information associated with a member;

registering a responding emergency medical system (EMS) profile using an EMS device, wherein the EMS profile includes one or more authorizations for receiving the member information associated with the member;

receiving, from the EMS device, trigger information including a request for the member information associated with the member;

receiving medical information associated with the member from one or more sources, wherein the medical information comprises non-standardized data;

converting the non-standardized data into standardized data, wherein the standardized data comprises one or more trends associated with treatments or conditions associated with the member, wherein converting the non-standardized data into the standardized data comprises:

identifying entities associated with one or more medically significant conditions based on utilizing machine learning to scan through the non-standardized data;

performing diagnoses based on the identified entities to determine the one or more medically significant conditions associated with the member; and determining the one or more trends based on the identified entities, the one or more medically significant conditions, and a personal health record associated with the member;

based on the request for the member information being valid, generating, using the standardized data, a member care file comprising updated member information, wherein the updated member information includes the one or more trends; and providing the member care file to the EMS device in real time so that a user of the EMS device has immediate access to the member care file.

20. The non-transitory computer-readable medium of claim 19, wherein the non-standardized data comprises non-standardized medical claims and medical records, and wherein the member information further includes at least one of medical history, medical insurance, work address, home address, provider preferences, medication, and vital signs.

* * * * *